(12) United States Patent
Lee

(10) Patent No.: US 8,529,078 B2
(45) Date of Patent: Sep. 10, 2013

(54) MIST LAMP

(76) Inventor: Huan-Ping Lee, Toufen Township, Miaoli County (TW)

(*) Notice: Subject to any disclaimer, the term of this patent is extended or adjusted under 35 U.S.C. 154(b) by 312 days.

(21) Appl. No.: 13/116,014

(22) Filed: May 26, 2011

(65) Prior Publication Data

US 2012/0300433 A1 Nov. 29, 2012

(51) Int. Cl.
*F21V 33/00* (2006.01)

(52) U.S. Cl.
USPC ............. 362/96; 362/101; 362/351; 222/113

(58) Field of Classification Search
USPC ......... 362/96, 101, 154, 351, 311.01–311.05, 362/643, 234, 253, 363, 355–357, 806, 811; 222/113; 73/36; 40/406, 441
See application file for complete search history.

(56) References Cited

U.S. PATENT DOCUMENTS

| 6,676,271 | B2* | 1/2004 | Kohn et al. | 362/101 |
| 7,690,533 | B2* | 4/2010 | Stilley | 222/113 |
| 2004/0218402 | A1* | 11/2004 | Jao | 362/555 |
| 2009/0166378 | A1* | 7/2009 | Stilley | 222/113 |

* cited by examiner

*Primary Examiner* — Bao Q Truong
(74) *Attorney, Agent, or Firm* — Leong C. Lei

(57) ABSTRACT

A mist lamp comprises a base, a container for storing a liquid, a mist generator, a shade, a light module, and a circuit board. The container is adapted to be mounted to the base. The mist generator is fitted into an opening of the container for converting the liquid into mist. The shade is located around the container and mounted to the base, the shade defining a hole communicated with an outlet of the mist generator such that mist converted in the container by the mist generator can be delivered to the ambient through the hole. The light module is adapted to be mounted in a recess of the base. The circuit board is adapted to be mounted in the recess of the base and electrically connected with the light module and the mist generator for controlling operations of the light module and the mist generator.

10 Claims, 8 Drawing Sheets

MIST LAMP

TECHNICAL FIELD OF THE INVENTION

The present invention relates to a mist lamp and, more particular, to a lamp that can output mist together with light to product a visual effect and an olfactory effect.

DESCRIPTION OF THE PRIOR ART

As commonly known, many essential-oil spraying devices employ a ultrasonic transducer to generate countless tiny vapor bubbles, due to vacuum, so as to release fine droplets of liquid or mist into ambient air. However, general essential-oil spraying devices cannot emit light or is constructed of opaque material, thus they cannot produce a visual effect. As to decorative lamps, they only have a dull pattern of lighting and cannot produce a vivid visual effect.

In view of the foregoing, the applicant has contrived a device that can produce both of visual and olfactory effects to bring about a more pleasant environment.

SUMMARY OF THE INVENTION

The primary object of the present invention is to provide a mist lamp that lamp that can produce both of visual and olfactory effects to bring about a more pleasant environment.

Another object of the present invention is to provide a mist lamp that employs a light module of LED to save energy consumption and reduce carbon emission.

Still another object of the present invention is to provide a mist lamp that can provide an alcohol mist for sterilization.

Still another object of the present invention is to provide a mist lamp that can increase the humidity of a room to prevent respiratory diseases.

To achieve the above objects, the invention comprises a base, a container for storing a liquid, a mist generator, a shade, a light module, and a circuit board, in which:

the container is adapted to be mounted to the base;

the mist generator is fitted into an opening of the container for converting the liquid into mist;

the shade is located around the container and mounted to the base, the shade defining a hole communicated with an outlet of the mist generator such that mist converted in the container by the mist generator can be delivered to the ambient through the hole;

the light module is adapted to be mounted in a recess of the base; and the circuit board is adapted to be mounted in the recess of the base and electrically connected with the light module and the mist generator for controlling operations of the light module and the mist generator.

Preferably, the invention may further comprise a sleeve to mount the container with the base.

Preferably, the light module is a unit comprised of light emitting diodes (LED) or cold cathode fluorescent lamps (CCFL).

Preferably, the liquid can be of pure water, alcohol, aromatic substance, perfume, fragrance oil, or essential oil or a combination thereof.

Preferably, the base is made of wood, ceramics, glass, plastic or fiberglass.

Preferably, the shade is made of ceramics, glass, plastic or fiberglass.

Preferably, the container is made of glass, plastic or fiberglass.

Preferably, the electrical power is supplied from a USB device or a general power supply.

Preferably, the sleeve is made of glass, plastic or fiberglass.

According to the technical means of the present invention, the mist lamp can produce both of visual and olfactory effects without too much consumption of electrical power, whereby the ambient air of a room can be sterilized to remove pathogens, the combination of the visual and olfactory effects can bring about a more pleasing environment.

Other objects, advantages, and novel features of the present invention will become more apparent from the following detailed description when taken in conjunction with the accompanying drawings.

DETAILED DESCRIPTION OF THE PREFERRED EMBODIMENTS

To allow the features, advantages and the effects of the present invention to be more easily understood, a detailed description in conjunction with the accompanying drawings will proceed in the following paragraphs.

Figure 1:
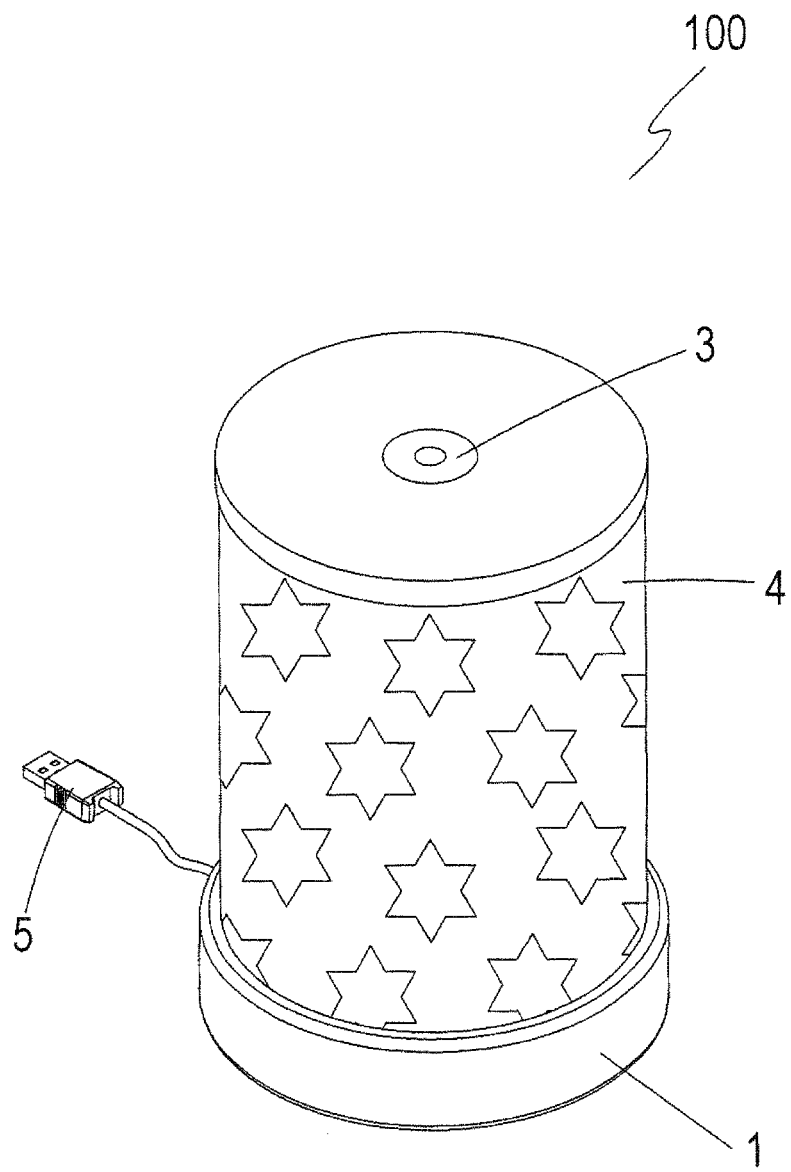
FIG. 1 is a 3-dimensional view of the present invention.
Figure 2:
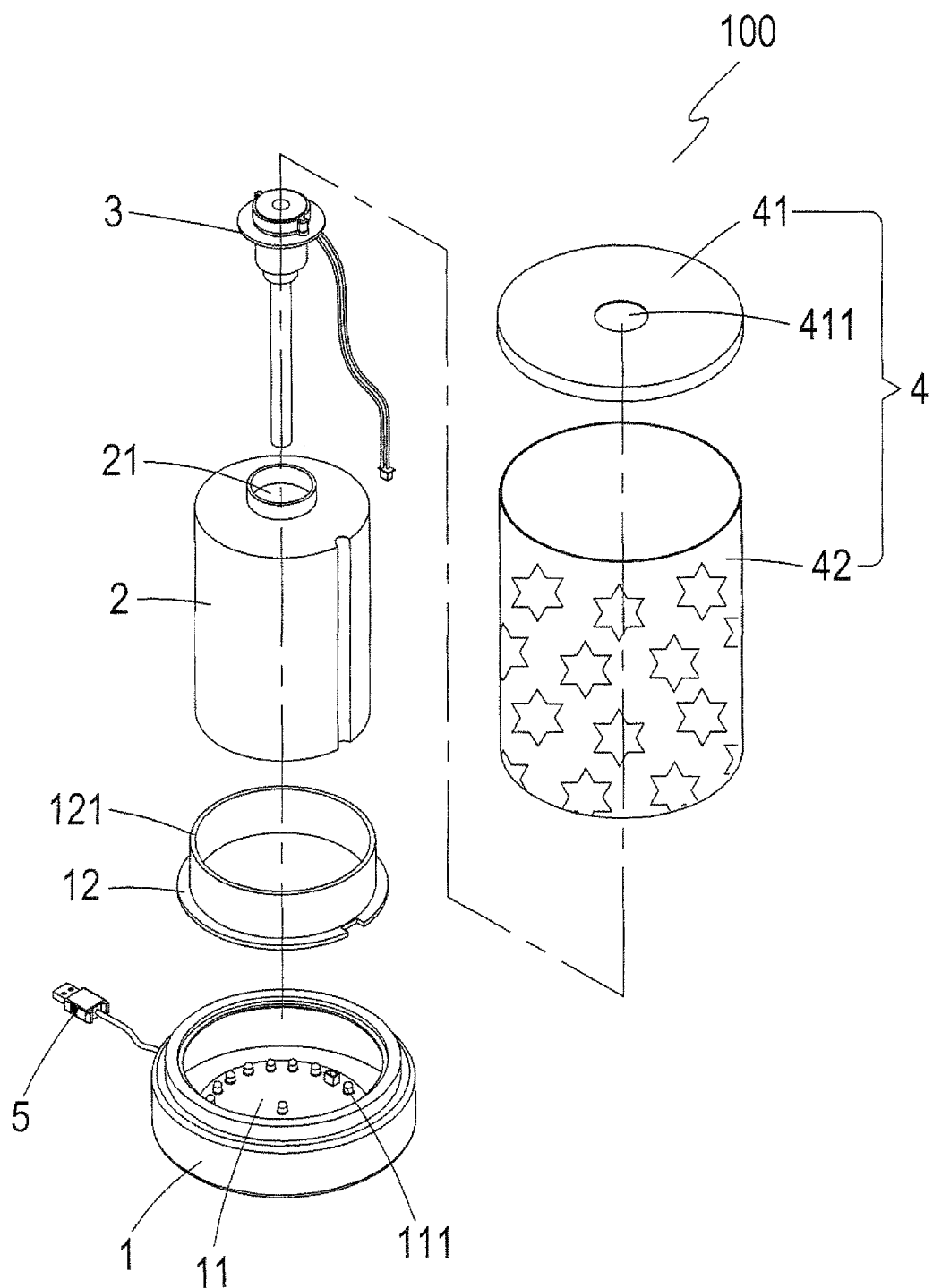
FIG. 2 is an exploded view of the present invention.
Figure 3:
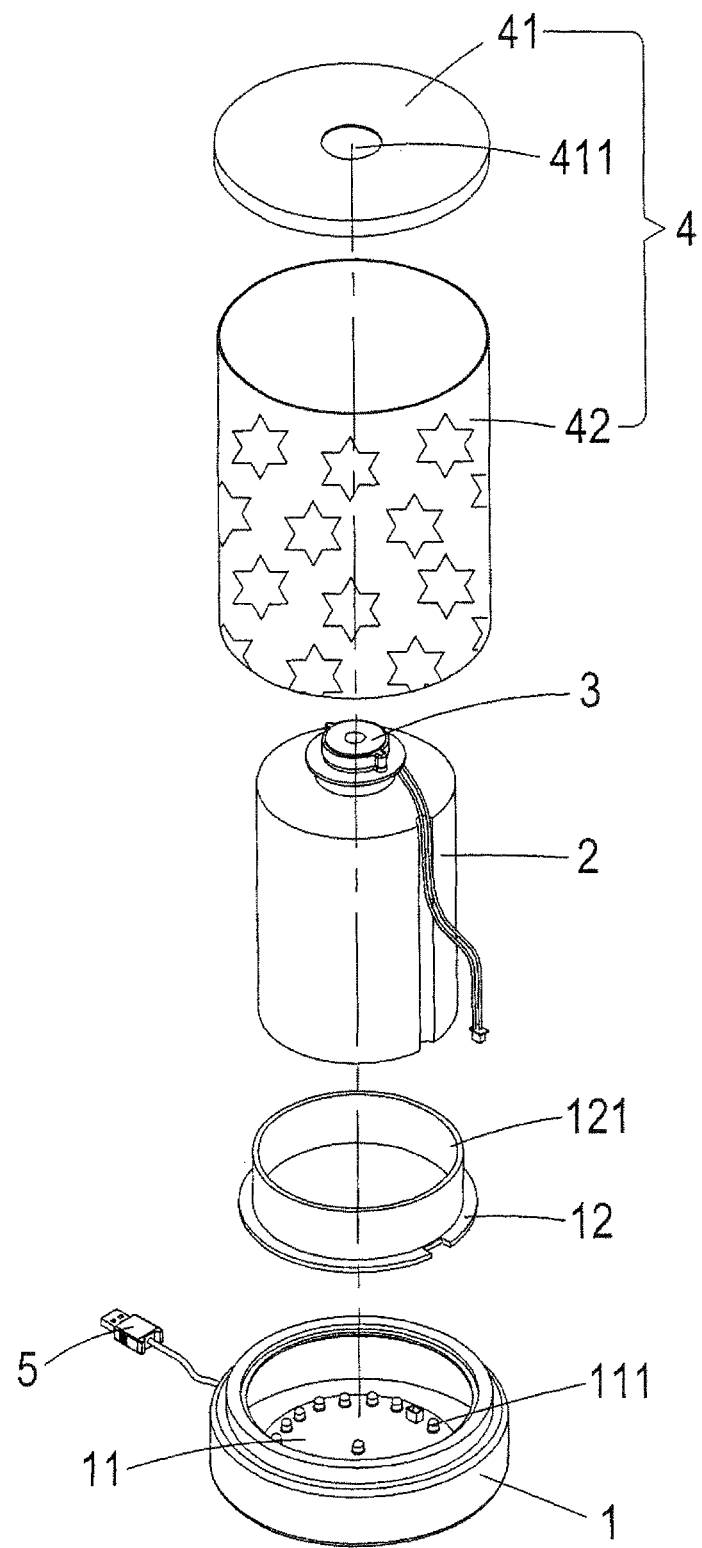
FIG. 3 is a partially exploded view of the present invention.
Figure 4:
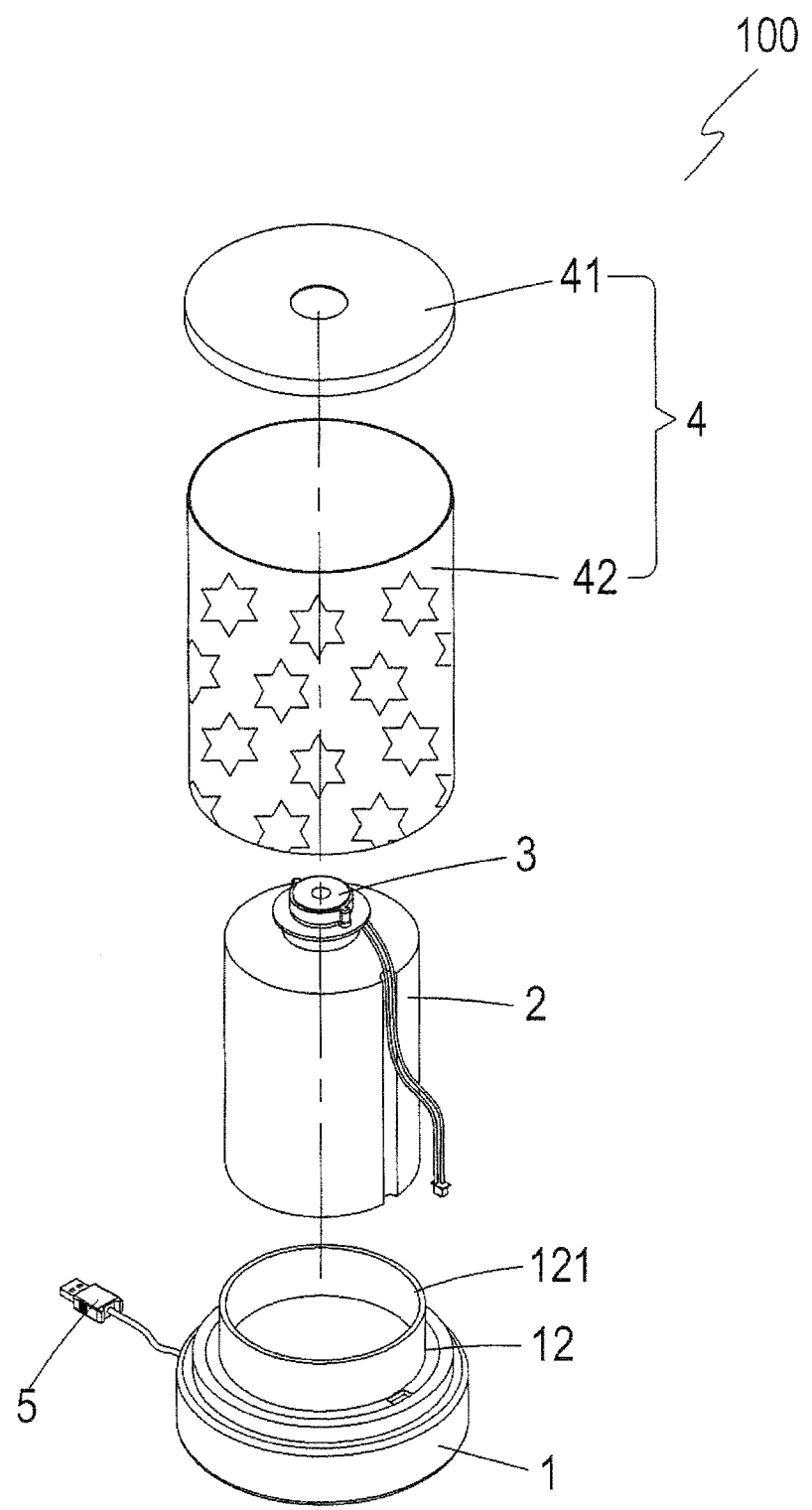
FIG. 4 is a partially exploded view of the present invention.
Figure 5:
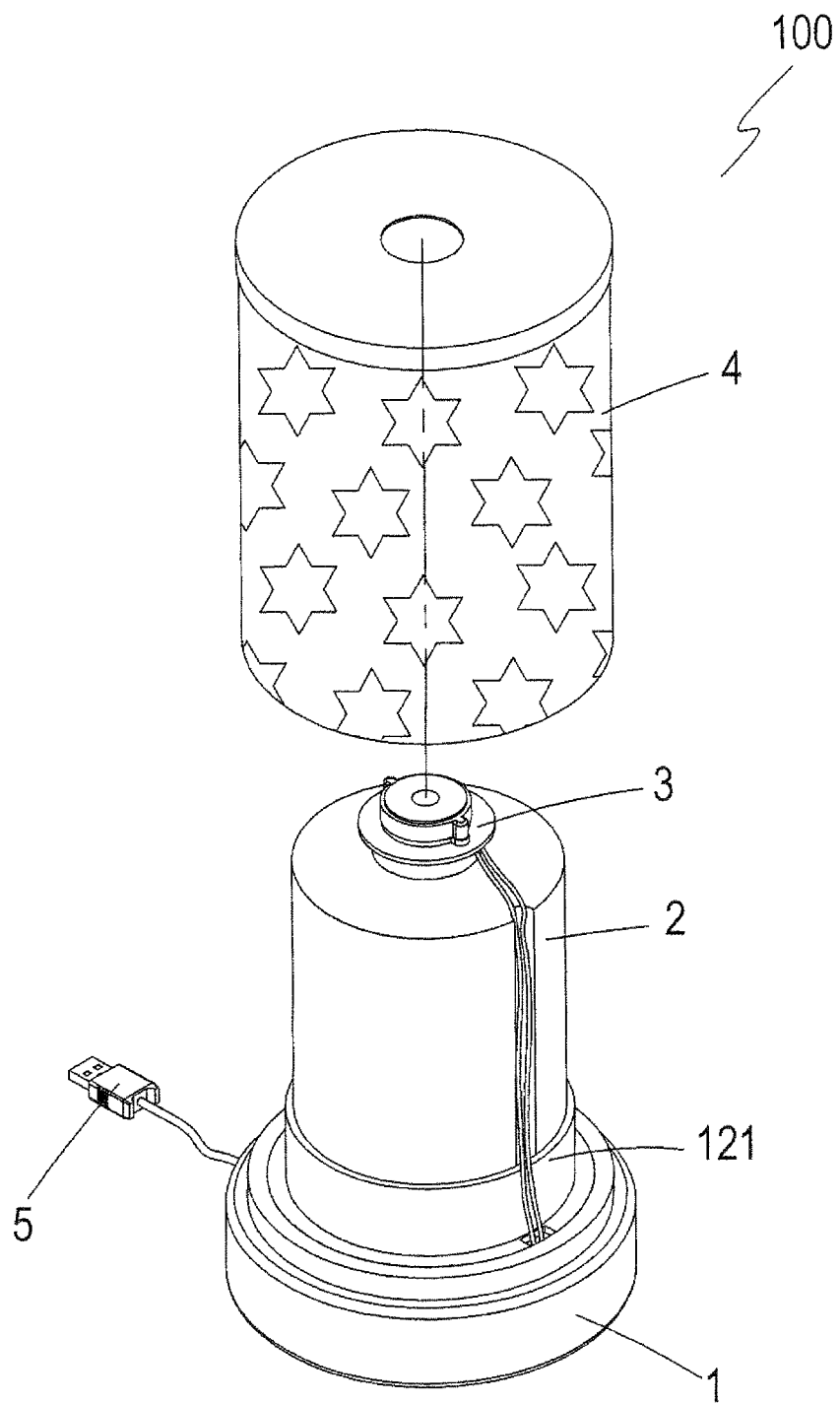
FIG. 5 is a partially exploded view of the present invention.

Referring to FIG. 1, a mist lamp 100 according to the present invention comprises a base 1, a container 2 for storing liquid (see FIG. 2), a mist generator 3, a shade 4, a light module 111 (see FIG. 2), a circuit board 11 (see FIG. 2), and a power supply connector 5.

As shown in FIGS. 2-5, the light module 111 can be mounted on the circuit board 11, which is mounted in a recess of the base 1. The base 1 can be made of wood, ceramics, glass, plastic or fiberglass. The light module 111 can be a unit comprised of plural light emitting diodes (LED) or cold cathode fluorescent lamps (CCFL). A sleeve 12 can be employed to mount the container 2 with the base 1. The sleeve 12 is mounted in the recess of the base 1 above the circuit board 11. The sleeve 12, being made of transparent material such as plastic, glass or fiberglass, has a circumferential portion 121 that can envelope a bottom portion of the container 2 to fix the container 2.

The container 2, being preferably made of transparent material such as plastic, glass or fiberglass, is mounted to the base 1 by way of the sleeve 12, in which the sleeve 12 is mounted to the base 1, and the container 2 is mounted to the sleeve 12. The container 2 is formed with a neck defining an opening 21 therein, into which the mist generator 3 is fitted for converting liquid in the container 2 into mist. The electrical power required for the light module 111, the mist generator 3, and the circuit board 11 can be supplied from a USB device or a general power supply.

The shade 4 is composed of an outer shell 42 and a top cover 41, in which the outer shell 42 is provided with a transparent pattern and has a dimension sufficient to surround the container 2, the top cover 41 defines a hole 411 therein. The shade 4 is located around the container 2 and mounted to the base 1, in which the hole 411 is communicated with an outlet of the mist generator 3 such that the mist converted in the container 2 by the mist generator 3 can be delivered to the ambient through the hole 411. Furthermore, the circuit board 11 is electrically connected with the light module 111 and the mist generator 3. The container 2 can be defined with an elongated groove, and the sleeve 12 can be defined with a cutout, to facilitate a wiring between the mist generator 3 and the circuit board 11.

Accordingly, the light emitted from the module light 111 on the circuit board 11 can be directed upwardly into the container 2 through the transparent sleeve 12 to enable the container 2 to emit light.

Figure 6:
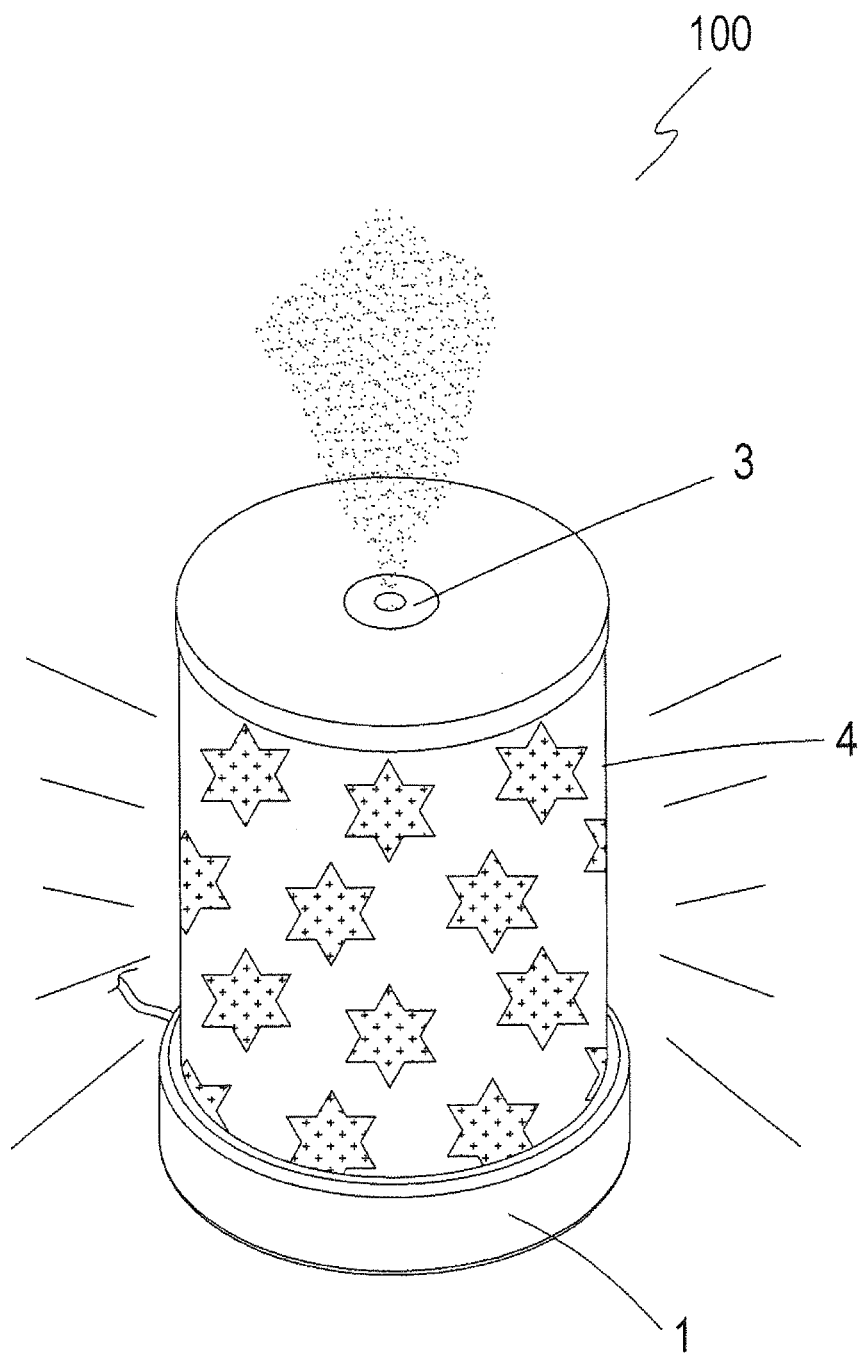
FIG. 6 illustrates an operation of the present invention.

In operation, as shown in FIG. 6, the light can emit out of the shade 4 with a pattern corresponding to the transparent pattern formed on the outer shell 41 of the shade 4. The mist converted in the container 2 by the mist generator 3 can be delivered to the ambient through the hole 411. The liquid stored in the container 2 can be of pure water for increasing the humidity of a room, alcohol or sterilization solution for sterilization, or either of essential oil, fragrance oil, perfume, or aromatic substance for spreading fragrance.

Figure 7:
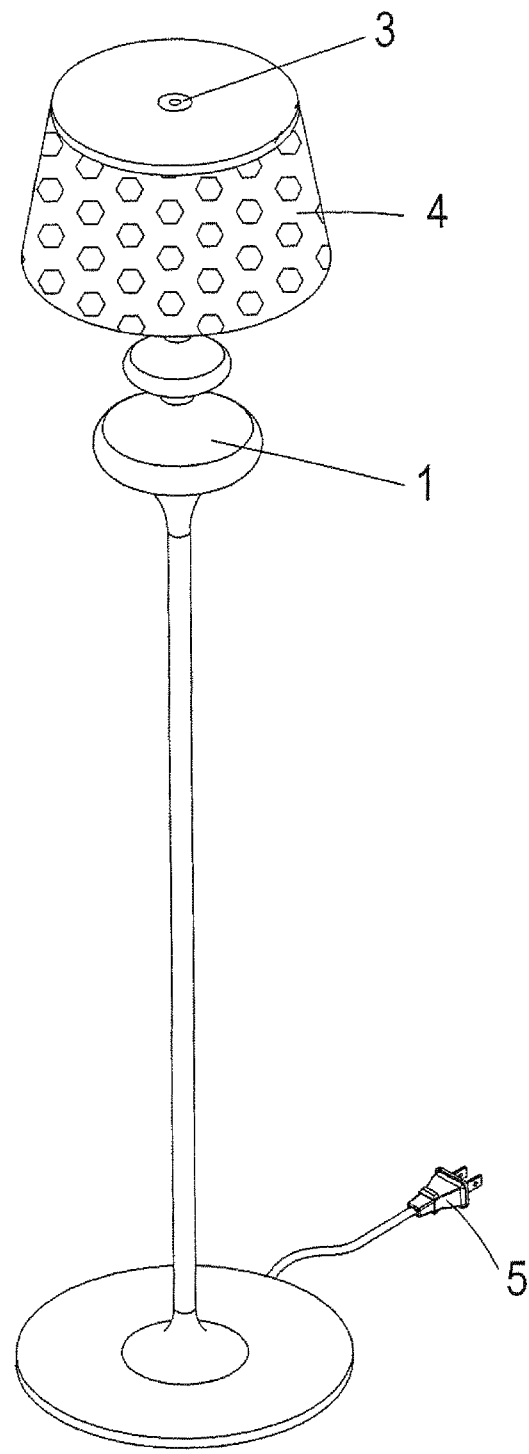
FIG. 7 shows a modified application of the present invention.
Figure 8:
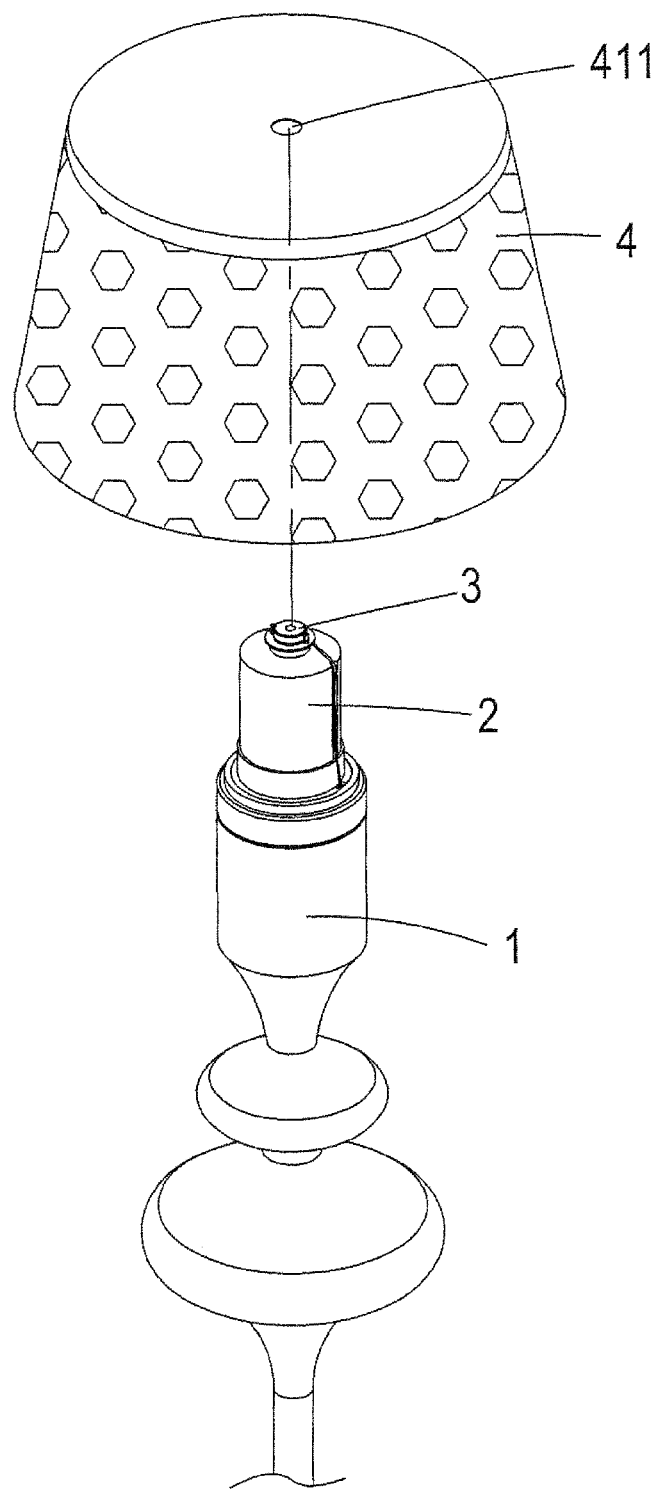
FIG. 8 shows an enlarged fragmentary view of the modified application of the present invention.

FIGS. 7 and 8 show a modified application of the present invention, in which the shade 4 is modified to be a cone-shaped one, and the base 1 is modified to an elongated support so that a floor lamp is formed.

Although the description above contains many specificities, these should not be construed as limiting the scope of the embodiments but as merely providing illustrations of some of the presently preferred embodiments. For example, the present invention can employ a plurality of containers respectively for a plurality of mist generators, which can be controlled by a circuit board alternately. The containers can be stored with different liquids, such as pure water, alcohol, sterilization solution, essential oil or the like. Thus, the scope of the embodiments should be determined by the appended claims and their equivalents, rather than by the examples given.

In view of the foregoing, the present invention is not only innovative in technical thoughts but also having several advantages over prior art. It is believed that the present invention is a novel design with innovative steps. An early and favorable action is respectfully solicited.

I claim:

1. A mist lamp comprising:
   a base;
   at least one container for storing a liquid, adapted to be mounted to said base;
   a mist generator fitted into an opening of said container for converting the liquid into mist;
   a shade located around said container and mounted to said base, said shade defining a hole communicated with an outlet of said mist generator such that mist converted in said container by said mist generator can be delivered to the ambient through said hole;
   a light module adapted to be mounted in a recess of said base; and
   a circuit board adapted to be mounted in the recess of said base and electrically connected with said light module and said mist generator for controlling operations of said light module and said mist generator.

2. The mist lamp of claim 1, further comprising a sleeve, wherein said container is mounted to said base by way of said sleeve, said container being mounted to said sleeve, said sleeve being mounted to said base.

3. The mist lamp of claim 2, wherein said container and said sleeve are both made of transparent materials, said shade is provided with a transparent pattern such that light emitted from said module light can be directed upwardly into said container through said sleeve to enable said container to emit light with a pattern.

4. The mist lamp of claim 3, wherein said light module is a unit comprised of at least one light emitting diode (LED) or cold cathode fluorescent lamp (CCFL).

5. The mist lamp of claim 4, wherein the liquid stored in said container can be of pure water, alcohol, aromatic substance, perfume, fragrance oil, or essential oil or a combination thereof.

6. The mist lamp of claim 1, wherein said base is made of wood, ceramics, glass, plastic or fiberglass.

7. The mist lamp of claim 1, wherein said shade is made of ceramics, glass, plastic or fiberglass.

8. The mist lamp of claim 3, wherein said container is made of glass, plastic, or fiberglass.

9. The mist lamp of claim 5, wherein electrical power required for said light module, said mist generator, and said circuit board is supplied from a USB device or a general power supply.

10. The mist lamp of claim 3, wherein said sleeve is made of glass, plastic or fiberglass.

* * * * *